United States Patent
Tsur et al.

(10) Patent No.: US 11,579,343 B2
(45) Date of Patent: Feb. 14, 2023

(54) METHOD AND APPARATUS THAT PROVIDE MATTE EFFECT WHILE ALLOWING HIGH RESOLUTION OUTPUT FROM A DISPLAY

(71) Applicant: PhoneOptika Ltd, Sde Warburg (IL)

(72) Inventors: Shraga Tsur, Tel Aviv (IL); Arie Heiman, Sde Warburg (IL)

(73) Assignee: PHONEOPTIKA LTD, Sde Warburg (IL)

( * ) Notice: Subject to any disclaimer, the term of this patent is extended or adjusted under 35 U.S.C. 154(b) by 511 days.

(21) Appl. No.: 16/052,779

(22) Filed: Aug. 2, 2018

(65) Prior Publication Data

US 2019/0041555 A1  Feb. 7, 2019

Related U.S. Application Data

(60) Provisional application No. 62/541,098, filed on Aug. 4, 2017.

(51) Int. Cl.
| | |
|---|---|
| *G02B 5/02* | (2006.01) |
| *G02B 5/20* | (2006.01) |
| *G02B 3/00* | (2006.01) |
| *G02F 1/1335* | (2006.01) |
| *G02B 27/00* | (2006.01) |

(52) U.S. Cl.
CPC ......... *G02B 5/0294* (2013.01); *G02B 3/0056* (2013.01); *G02B 5/021* (2013.01); *G02B 5/0215* (2013.01); *G02B 5/201* (2013.01); *G02B 27/0018* (2013.01); *G02F 1/133502* (2013.01); *G02B 2207/123* (2013.01); *G02F 1/133526* (2013.01)

(58) Field of Classification Search
CPC .... G02B 5/0294; G02B 3/0056; G02B 5/021; G02B 5/0215; G02B 5/0268; G02B 5/201; G02B 27/0018; G02B 2207/123; G02F 1/133502; G02F 1/133524; G02F 1/133526
See application file for complete search history.

(56) References Cited

U.S. PATENT DOCUMENTS

| | | | |
|---|---|---|---|
| 6,381,072 B1 * | 4/2002 | Burger | G02B 3/0056 359/621 |
| 2006/0050398 A1 * | 3/2006 | Gurevich | G02B 13/18 359/622 |

* cited by examiner

*Primary Examiner* — Wen Huang
(74) *Attorney, Agent, or Firm* — Reches Patent

(57) ABSTRACT

A method and an apparatus for providing a matte affect while enhancing an output of a display that comprises multiple display pixels, the apparatus may include a first array of microlenses that is configured to scatter ambient light; a second array of microlenses; wherein first array of microlenses is parallel to the second array of microlenses; wherein microlenses of the first array of microlenses and the microlenses of the second array have a dimension of tens of microns; and wherein the first array of microlenses and the second array of microlenses are shaped and positioned to pass through the image from the display, when the apparatus is attached to the display.

16 Claims, 23 Drawing Sheets

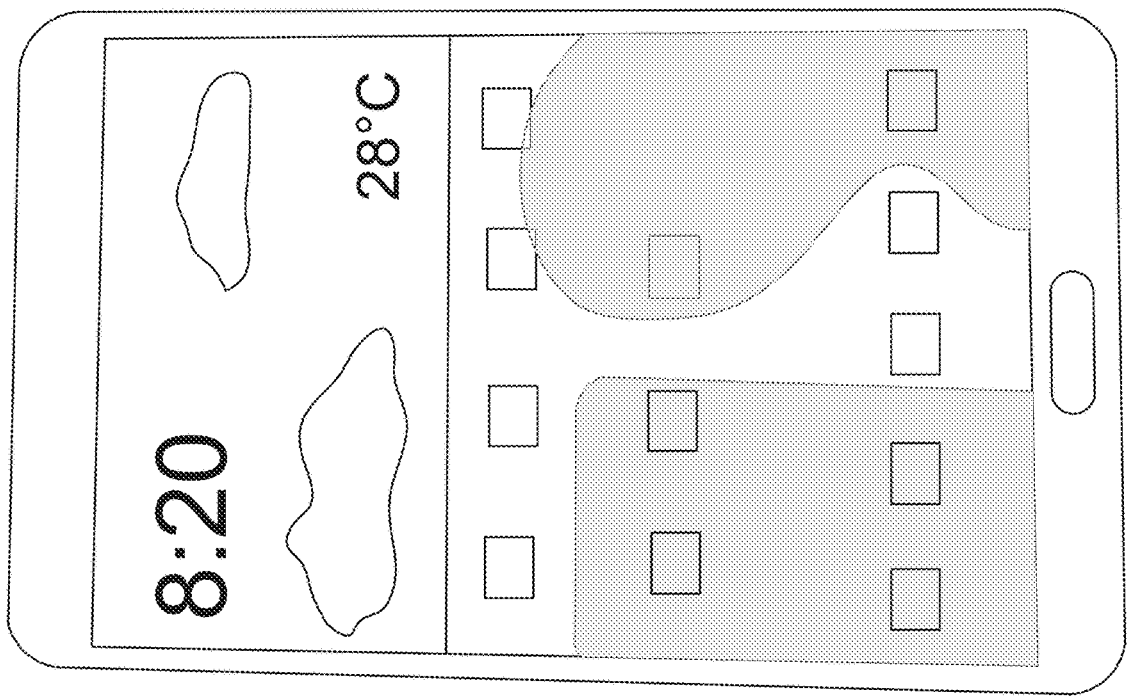
PRIOR ART
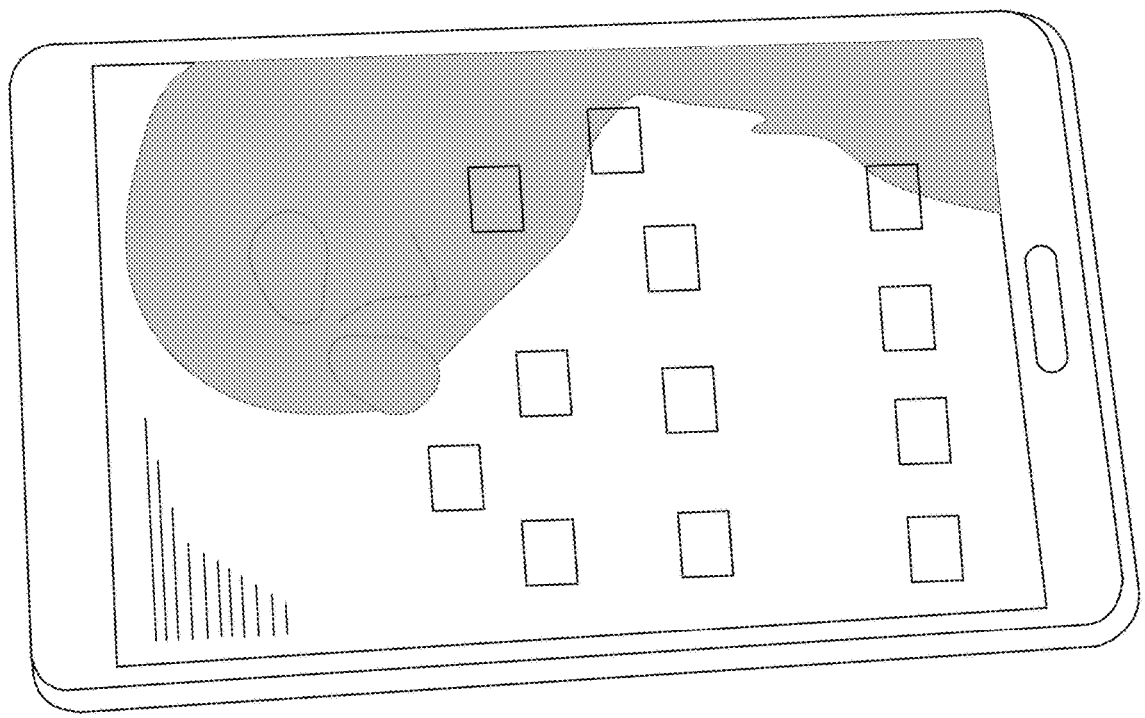
FIG. 1

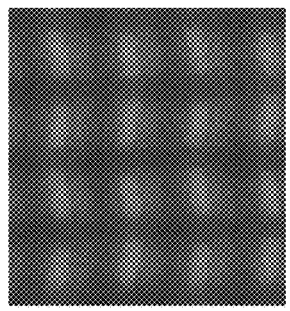
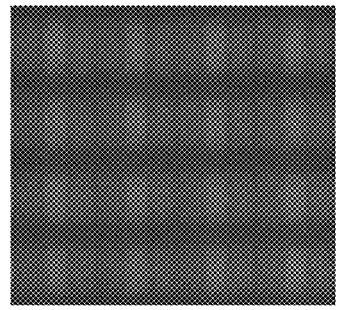
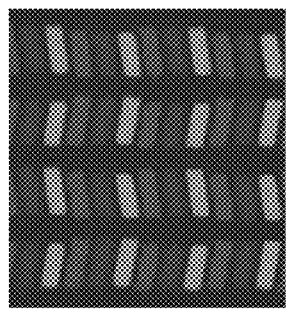
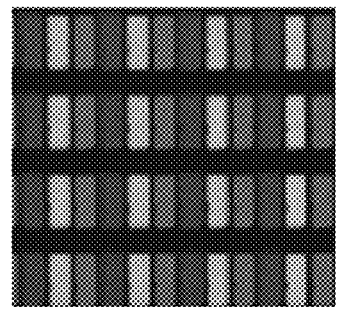
FIG. 3

Display contrast enhancement:

Units:

$\text{mrad} := 10^{-3} \cdot \text{rad} \qquad \mu m := 10^{-3} \cdot mm$

Current contrast:

$Ib := 0lx, 10lx .. 100000lx$ — Ambient illuminance $Rd := 4.6\%$ — iPhone 6 reflectance $Bd := 558 \frac{cd}{m^2}$ — iPhone 6 max. display brightness $C0(Ib) := \frac{Bd}{\pi \cdot Rd \cdot Ib}$ — Current max. contrast $Cm := 1$ — Minimal required brightness (empirical)

FIG. 7

100 watt bulb point source reflected from the cover glass of a typical mobile phone:

$P_b := 1500 \text{lm}$     100 Watt bulb luminous flux $\theta_e := 0.3 \text{ mrad}$    $\theta_e = 0.017 \text{ deg}$    Eye angular PSF $f_e := 20 \text{mm}$     Eye focal length $d_e := f_e \cdot \theta_e$    $d_e = 6 \cdot \mu m$    Retinal PSF diameter $D_e := 3 \text{mm}$     Eye pupil (Highlight) diameter $L := 1m, 1.1m .. 1000m$     Eye distance from the bulb (metres)

$$Ib(L) := \frac{P_b}{\pi (L \cdot \theta_e)^2} \qquad Ib(10m) = 5.305 \times 10^7 \cdot lx$$

Effective bulb point source image intensity on the eye $$Cd(L) := \frac{Bd}{\pi \cdot Rd \cdot Ib(L)}$$

Display contrast against the reflected image of the bulb

FIG. 8

100 watt bulb point source reflected from the cover glass of a typical mobile phone but with a matte lens-array:

Assume:

$1/f = (n-1)(1/R1 - 1/R2)$
$R2 = \infty$
$\Rightarrow R = (n-1)f$      Lensmaker equation $n := 1.5$      Refractive index of the outer lens-array material $C := 10\mu m, 11\mu m .. 1000\mu m$      Outer lens-array focal length parameter $R_c(C) := (n-1) \cdot C$      Outer lens-array radius of curvature $Dc := 10\mu m, 11\mu m .. 200\mu m$      Lens size parameter $\Theta m(C, Dc) := 4 \cdot \operatorname{atan}\left[\dfrac{Dc}{2(n-1) \cdot C}\right]$      The bulb as an extended source with an effective angular size of $2^*\Theta m$ (Matte)

$Cdm(L, C, Dc) := Cd(L) \cdot \left(\dfrac{2 \cdot \Theta m(C, Dc)}{\theta e}\right)^2$      Display contrast with matte lens-array

FIG. 9

500 watt ball lamp extended source reflected from the cover glass of a typical mobile phone but with a matte lens-array:

$Pl = 7500\text{lm}$ — Lamp luminous flux $Rl = 20\text{cm}$ — Lamp radius $\Theta_{m}(C, Dc) = 4 \cdot \text{atan}\left[\dfrac{Dc}{(n-1) \cdot fl}\right]$ — Each point on the lamp image is an extended source with an effective angular size of 2·Θm (Matte)

$Il(L, C, Dc) = \dfrac{Pl}{\pi \cdot (Rl + 2L \cdot \Theta_{m}(C, Dc))^2}$ — Effective lamp matte image intensity $Cdm\ell(L, C, Dc) = \dfrac{Bd}{\pi \cdot Rd \cdot Il(L, C, Dc)}$

FIG. 12

One dimensional ambient light reflected grey level step contrast image:

Assume:
- One dimensional (effectively) infinit contrast step in reflected ambient image from display covered with "matte lens array".
- The reflectin from the matte lens array smears out the border thus, reducing that contrast in the reflected image.
- The smear is 1 dimensional.
- The step function occures between two large constant brightness areas ==> No dipendence on range $$Ibc(Ib, C, Dc) = Ib \cdot \left( \frac{\theta e}{2 \, \theta m(C, Dc) + \theta e} \right)$$

Ambient step-contrast as function of lens-array parameters $$Cbm(Ib, C, Dc) = \frac{Bd}{\pi \cdot Rd \cdot Ibc(Ib, C, Dc)}$$

Display contrast with lens-array matte effect for a 1 dimensional reflected ambient step-contrast

FIG. 15

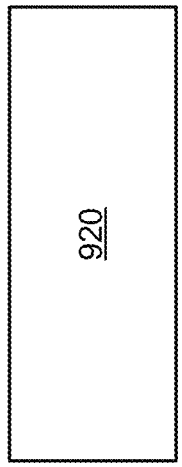
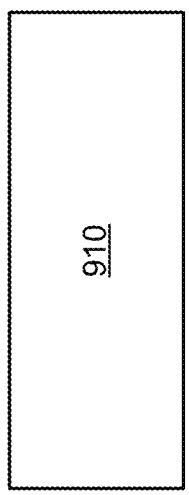
FIG. 23

METHOD AND APPARATUS THAT PROVIDE MATTE EFFECT WHILE ALLOWING HIGH RESOLUTION OUTPUT FROM A DISPLAY

CROSS REFERENCE

This application claims the priority of US provisional patent 62/541,098 filing date Aug. 4, 2018.

BACKGROUND

Today digital displays are very popular. They are used in mobile phones, smart phones, wearable devices, tablets, computers, TV, cars, digital camera, etc. However, in some cases the user encounters challenges that reduce significantly his viewing experience.

SUMMARY

There may be provided an apparatus and method for providing Matte effect while allowing high resolution output from a display.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1 illustrates prior art displays;

FIG. 3 is an example of prior art displays with prior art anti-glare covers;

FIG. 7 presents the calculation of the contrast of the display at the presence of a reflected ambient image from the cover glass as function of ambient light intensity;

FIG. 8 presents the calculation of the contrast of the display from an image of a 100 watt bulb point source, reflecting from a typical cover glass;

FIG. 9 presents the formulas that control the contrast improvement;

FIG. 12 presents the formulas and calculations of the contrast of the display against the image of a 500 watt ball lamp, extended source reflecting from a cover glass with the apparatus as part of it;

FIG. 15 Present the formulas and calculations of the display contrast improvement at the border of a one dimensional ambient illumination step line reflecting from a cover glass with the apparatus;

FIG. 23 is an example of a method.

DETAILED DESCRIPTION OF THE DRAWINGS

In this application we will present a method and apparatus that improves significantly the user experience in the following case:

When a digital or analog display is used outdoors on a sunny day, it is almost impossible to see what is displayed on the screen, this is due to the glare of the sun and the strong ambient image that is reflected from its cover glass, blends into the displayed image and disrupts it.

Thus the displayed image has significantly lower contrast, below usability. We call it blindness of the display. As an example, in FIG. 1 we depict two typical displays of a mobile phone in outdoor on a sunny day and in indoor scenarios respectively.

This phenomenon occurs especially in mobile devices where the ambient light condition change significantly while their display brightness is limited, such as mobile phones, tablets, wearable device, displays in cars, navigation displays, Digital camera display, etc., that are used in indoor and outdoor scenarios, day and night.

In order to reduce the blindness effect of the display some people block the sun with their hand in order to improve the visibility of the display, but with little success. Popular Anti-Glare, matte finish screen protectors, diffuse the reflected ambient image but with little success and at the cost of reducing the resolution of the displayed image.

In addition, most of the displays use shiny, smooth specular reflective cover glasses, hence the display acts as a mirror and reflects, with some attenuation, almost all the objects that are in the front of the display, thus the user see a combination of two images, one is the desired image and a second image is the attenuated image of the background. In some cases it is very annoying to the user.

If one uses a simple matte finish screen as a display protector, it will scatter the ambient light and will reduce the effect of the reflected ambient light and the ambient image but with sacrificing the resolution of the displayed image.

There may be provided a method and apparatus that reduces the blindness effect and the mirror effect of the display by providing a special matte element that scatters the ambient light without sacrificing the resolution of the display image. Namely, for the ambient light the display acts as perfect matte display and for the displayed image, it acts as a transparent optical element that does not alter the displayed image to be seen by the user eye.

The apparatus can be embedded as an additional thin layer that is part of the display or can be used as an add-on transparent thin film that covers the display.

Figure 2:
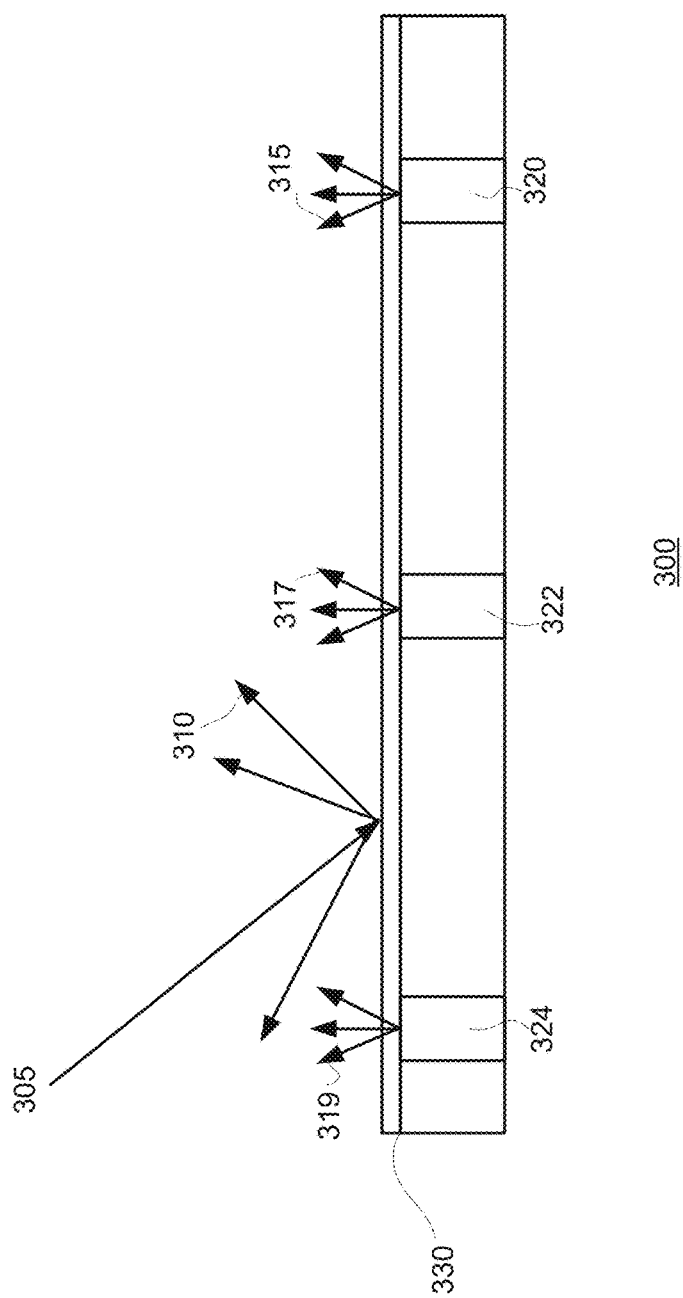
FIG. 2 illustrates reflected light and light emitted from various pixels of a prior art display.

A matte reflecting surface is diffusing the ambient light that impacts it. Such a matte surface can be achieved as an example, by using a material that undergoes special etching. A matte surface of a cover glass of a display reduces the contrast of the reflected ambient image at the cost of decreased contrast and blurring the display image itself. The distance between the displayed image source plane and the matte layer affects the amount of blurring of the displayed image. In FIG. 2 we present the diffusion model of a prior art apparatus and its effect on the reflected image of the ambient and on the displayed image.

Display 300 has only three color pixels: Red 324, Green 322 and Blue 320 and on the top of it there is a matt surface 330. Rays from each point of the ambient image 305, impact the matte surface 330 and are scattered and generate a diffused reflected ambient image and light 310. As the matte surface is symmetrical, the pixels of the display are also scattered. When the red pixel 324, impacts the matte material it is diffused and generates a diffuse red pixel light 319, the same happens to the green pixel 322 that generates the diffuse green pixel 317 and to the blue pixel 320 that generates the diffuse blue pixel 315. The diffuse effect reduces the luminance of the pixels as well as the pixels are blurred. As a result of the thickness of the cover glass and all the layers that are on top of the display pixels, the distance between the image source and the matte layer, affects the amount of blurring of the image, as the distance is bigger the images becomes more blurred. In FIG. 3 we present two enlarged portions of the pixels of displays of different mobile phones with and without a commercial matte cover. It is very noticeable that using a matte cover blurs the image of the display 405 compared to the original image 401 and same for image 505 which is much more blurred than the original image 501.

Varying levels of diffusion yield level of reducing glare. The more diffuse the panel surface the more glare reduction it provides. An inverse relationship exists between the degree of diffusion and the panel's resolution Due to the blur of the displayed image, current display manufacturers mostly use smooth, mirror-like display covers even though those strongly reflect the annoying ambient image on top of the displayed image. Manufacturers of matte "Anti-glare" display covers have to compromise and use "low matte" display covers in order to minimize the damage in resolution, contrast and "vividness" of the displayed colors. Thus, they lose both display contrast while the ambient reflected, unwanted image is still present and annoying.

There may be provided a method and apparatus that uses a special matte surface that strongly diffuses the ambient light but the displayed image is not diffused and its brightness, contrast and sharpness remain in the same level that is achieved without using the special matte element.

Figure 4:
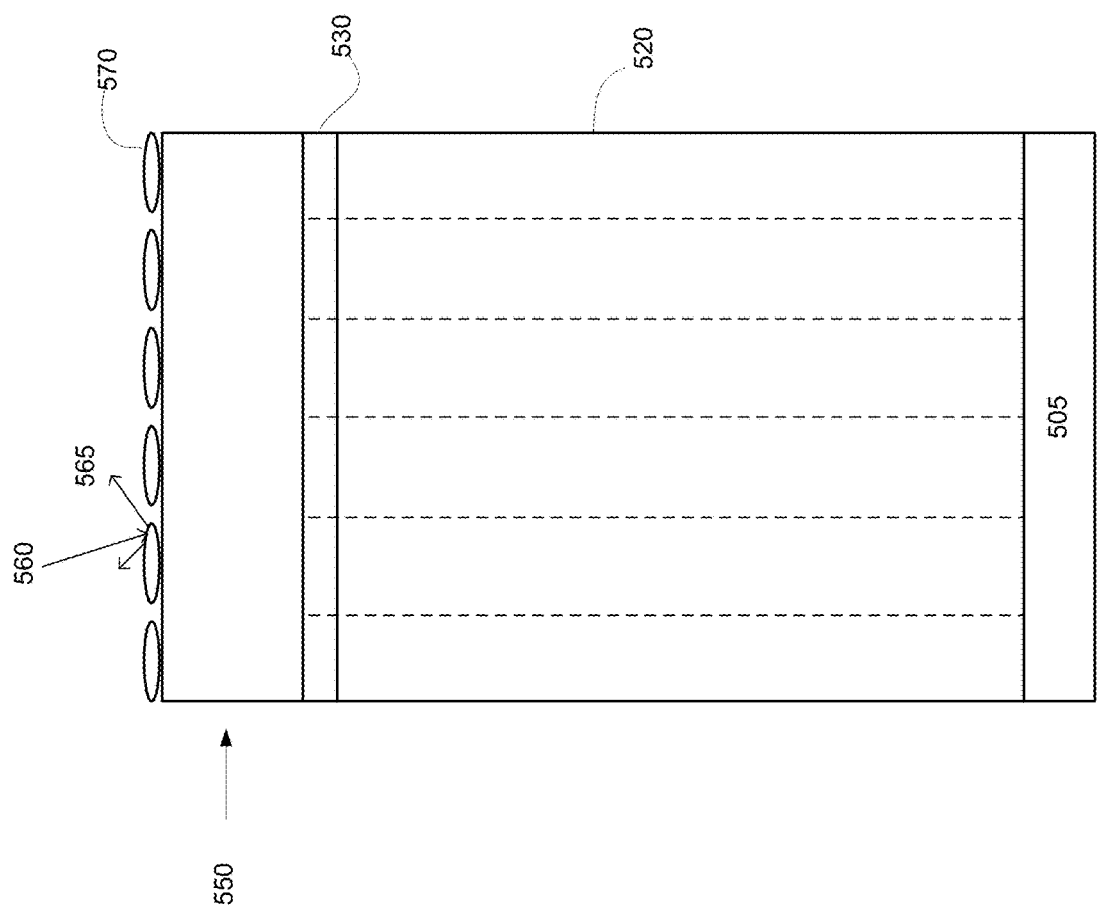
FIG. 4 is an example of an apparatus.
Figure 5:
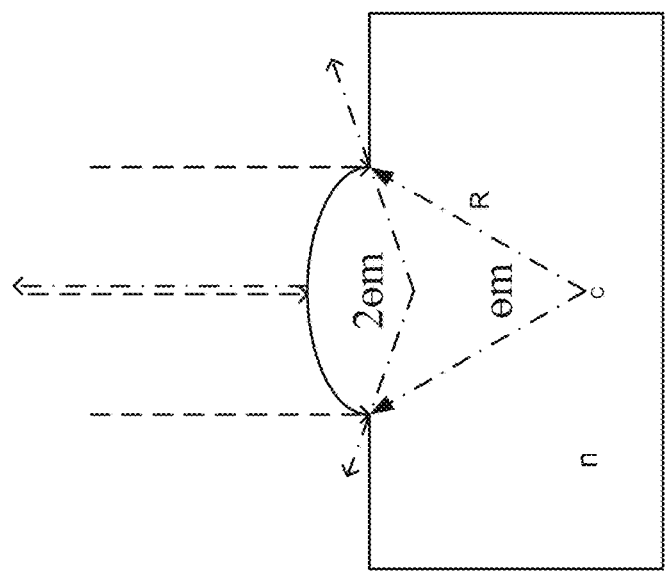
FIG. 5 is an example of light rays.

This is very attractive since the reflected ambient image and light are strongly diffused while the displayed image remains sharp and clear. The apparatus and system that is described in this application allow us to improve significantly the contrast of the display in the presence of a strong ambient light at the background without blurring the display image The suggested apparatus may include a thin material with a few layers. The material can be made as an example from transparent polymers, glass or any other transparent material. The upper layer may include an array of micro lens elements that cover the whole display. The outer spherical surface of each such micro lens may be convex or concave. Each lens element has dimension of tens of μm thus its size is below the resolution of the human eye. A typical size can be 50-100 μm. Parallel rays of distant ambient light and ambient images that are reflected off the outer spherical surface of each micro-lens are scattered and distributed in a cone angle that is twice the apex of the spherical surface see FIG. 5. An array of such micro lenses, each of them below the resolution of the eye, acts as a perfect and strong matte surface as can be seen in FIG. 4. As an example, when a ray 560 of ambient light impacts one of the lens of 570 it is scattered in various directions and generates multi rays 565 which are seen by the human eyes as a matte surface.

In order to keep the brightness and the resolution of the display we use a layer that is composed of an array of special micro optical element 550 that does not change the appearance of the display 505 nor its resolution.

FIG. 4 presents a cross section of two dimensional elements that are attached to the glass of a digital display. In FIG. 4 the pixels of the display are 505 which are attached to the bottom of the cover glass 520. The height (thickness) of the cover glass varies between different phone manufactures but it is in the range of ~1000-2000 μm. 530 is a transparent index matching glue/gel. The layer 550 is a two dimensional optical sub system that is attached bellow the outer layer of lenses 570. Layer 550 needs to be designed such that the pixels in display 505 will be reimage to the eye of the user without losing the brightness and the resolution. In a later paragraph we will present as an example five different subsystems of 550 with 570.

In FIG. 4 and various other figures the dashed lines that pass through the apparatus may illustrate optical paths or may just provide a delimitation between areas of the display that include a pixel and a surrounding of the pixel.

Getting Matte Effect with an Array of Micro Lenses

In this paragraph we present a simplified model and performance analysis of the matte effect that is generated by an array of micro lenses in the outer layer. The shape of a single lens, when viewed from above, may be a triangle, square, hexagon or any other shape such that an array of such elements covers the whole plane with no "dead" area between the lenses. The micro lens array layer can be made of a transparent polymer material, UV cured epoxy resins, transparent glass or any other transparent material. It can be an add-on attached to the display or embedded in the display.

The discussion is similar for convex and concave radii but, without loss of generality and for the simplicity of the analysis, we will relate to the convex case only.

Let us assume the following

1. The ambient image is reflected from the outer interface of each lens with air so we will concentrate our calculations as an example on this configuration.
2. Without loss of generality and for the simplicity of the calculations, assume a single spherical lens that geometrically, is a part of a sphere that has a radius R, has its center at C and a cone angle of $\theta m$ (FIG. 5).
3. Assume parallel rays that emerge from one point of a distant (relative to the dimensions of the lens), ambient source (infinity, for simplicity) that hit the outer, spherical surface, of that lens. Without loss of generality, assume that these light rays are parallel to the optical axis of the lens.
4. Using the laws of reflection: The incident angle relative to the radius (that is perpendicular to the surface of the lens) is equal to the reflected angle relative to the same radius. Thus the rays that hit the circumference of the lens, on both sides, form an angle of ½ $\theta m$ with the radius and therefor θm relative to the perpendicular optical axis of the lens. This happens along the whole circumference of the lens.

5. Thus the reflected rays from the lens form a cone angle (see FIG. 5) of 2θm and the outer surface of the lens acts as convex mirror with a reflectance of ~4%, similar to that of glass (depending on the exact refractive index of the material of the lens).
6. To the viewer, the reflected image of a distant point source will be a point source emerging from the focus of the minor that is located at ½R from its center.
7. The reflected light from each micro-lens will seem as a small point source, at its focus so the array of the outer surfaces of the micro-lenses will reflect and split each point source in the ambient image to an array of tiny point sources.
8. As the separation between adjacent such sources is below the resolution of the human eye, all these point sources will combine into one even matte surface that perfectly scatters the light of the distant point source.

In order to evaluate the matte performance we calculate the amount of smear and contrast reduction of the micro-lens array, relative to the reflection from the plane mirror-like surface of the cover glass of the display. Let us assume the following:

A point source emitting a radiative power Ps into a solid angle of 4π sRad thus, its brightness is $$Bs = \frac{Ps}{4\pi}$$

Figure 6:
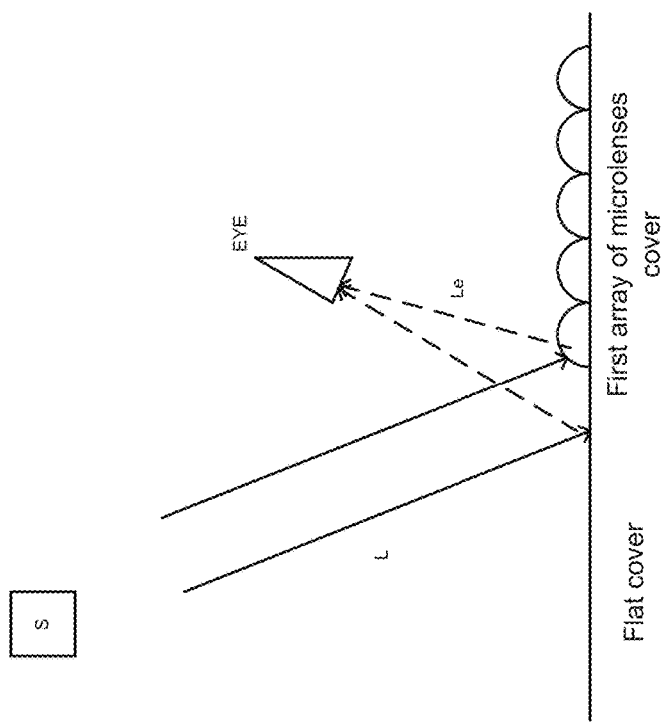
FIG. 6 presents the parameters that serve as the basis to the calculations of a contrast enhancement of the display where a light point source is reflected from its cover glass to the eye of the observer.
Figure 10:
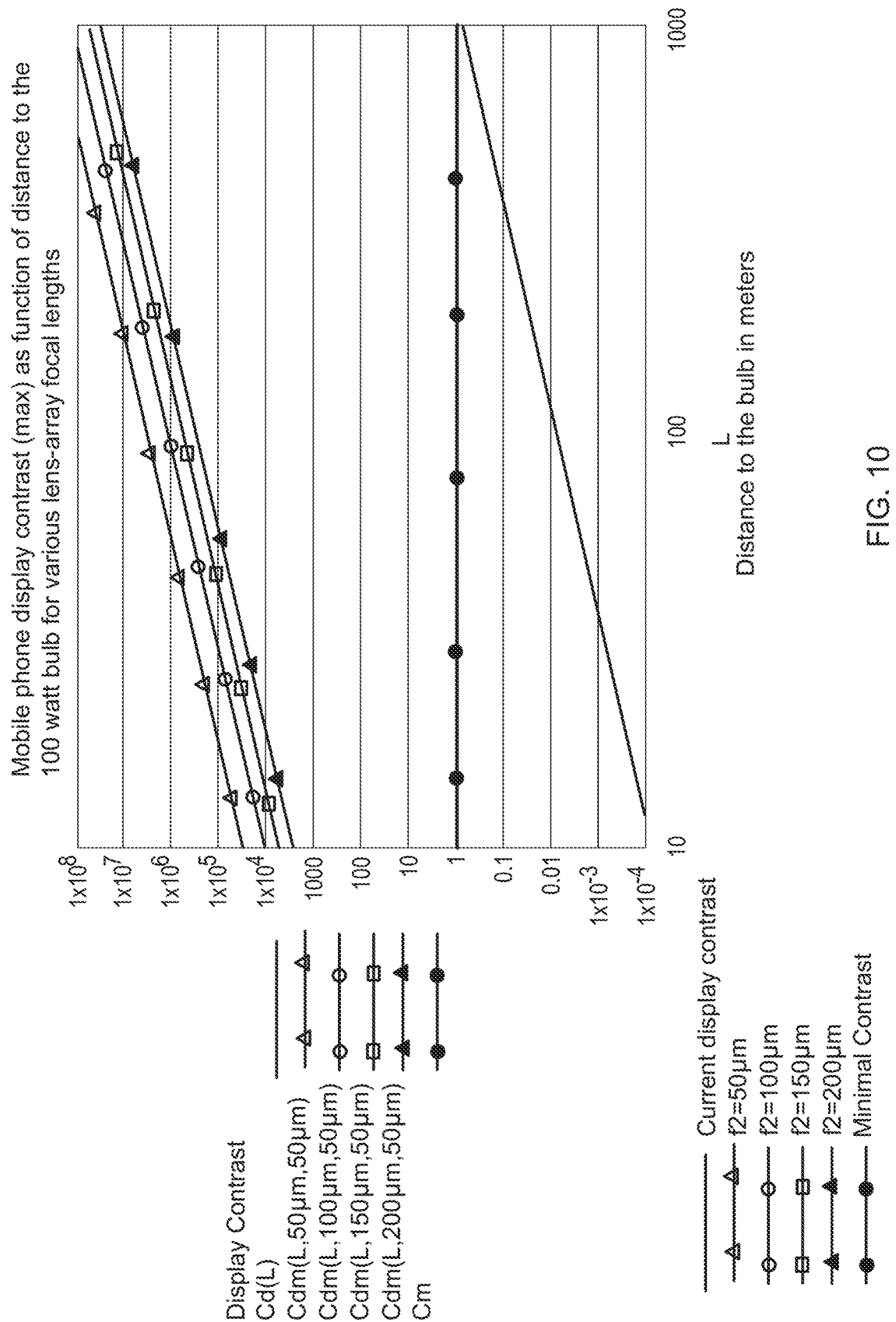
FIG. 10 presents the contrast as a function of the distance L to the bulb for various focal lengths f2 of the outer lens array.
Figure 11:
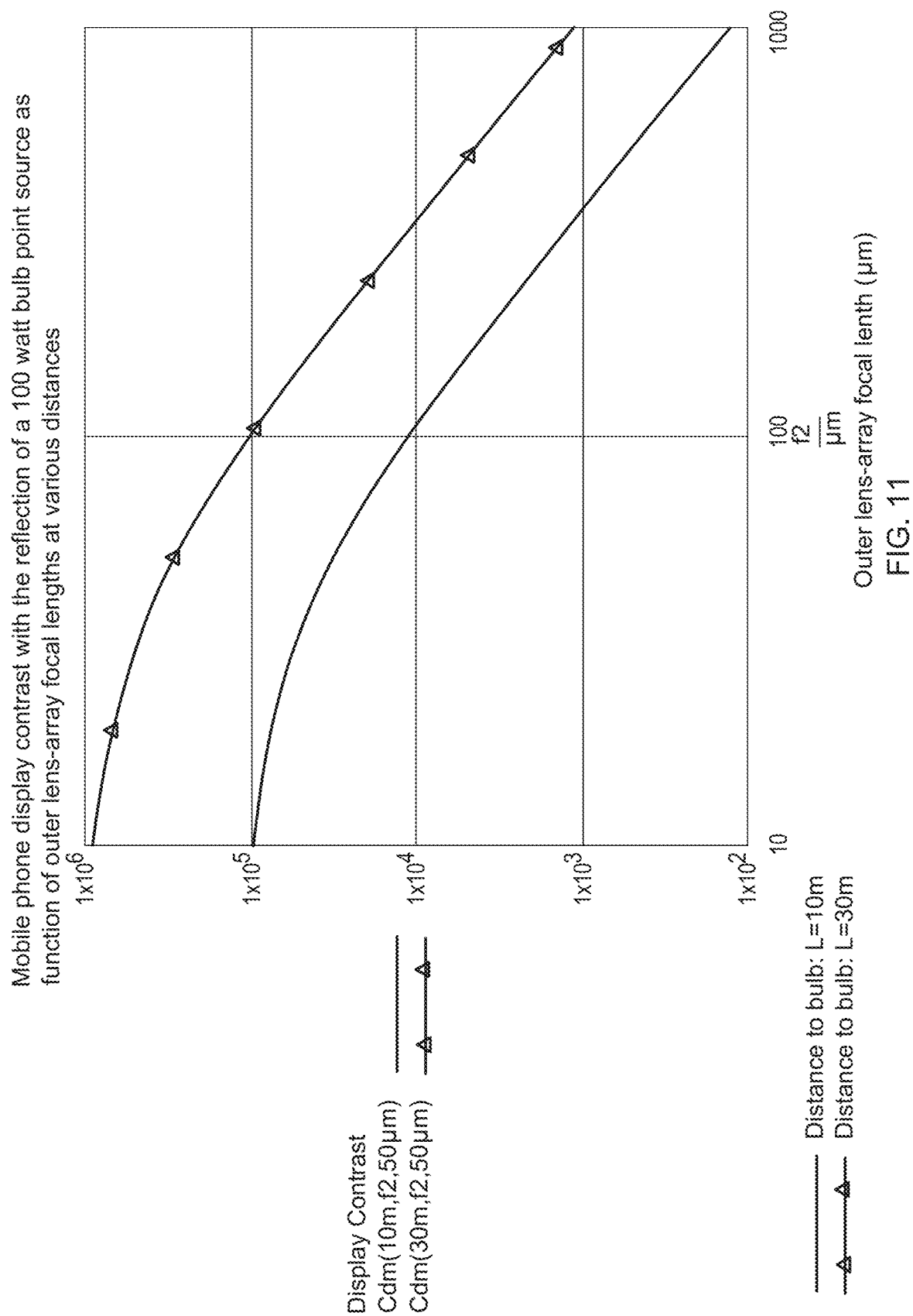
FIG. 11 presents the display contrast with the reflection of the bulb point source as function of the outer lens array focal length f2, for various distances of the source.
Figure 13:
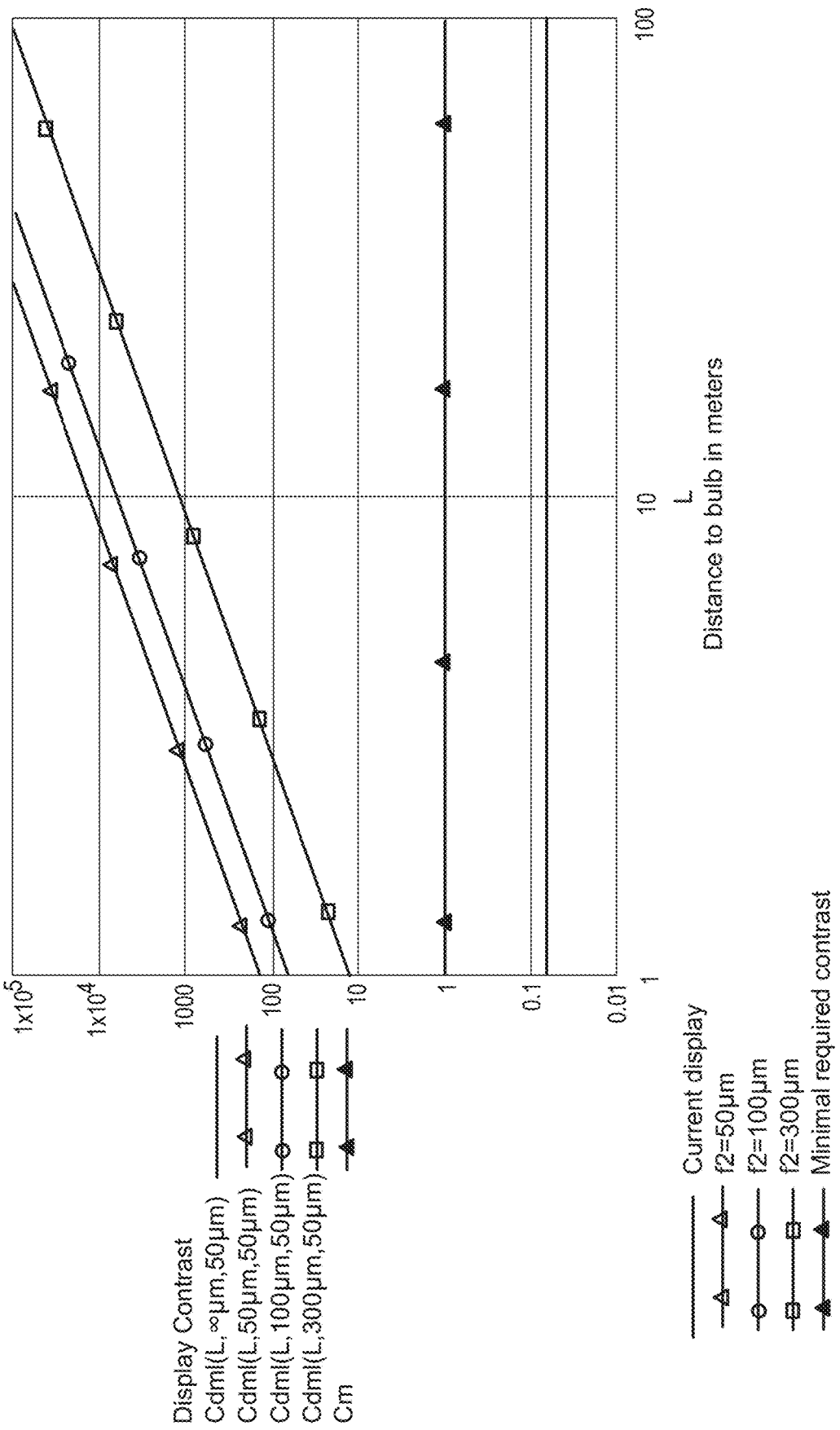
FIG. 13 presents the contrast improvement on the reflected image of the 500 watt extended source as a function of L for various value of f2.
Figure 14:
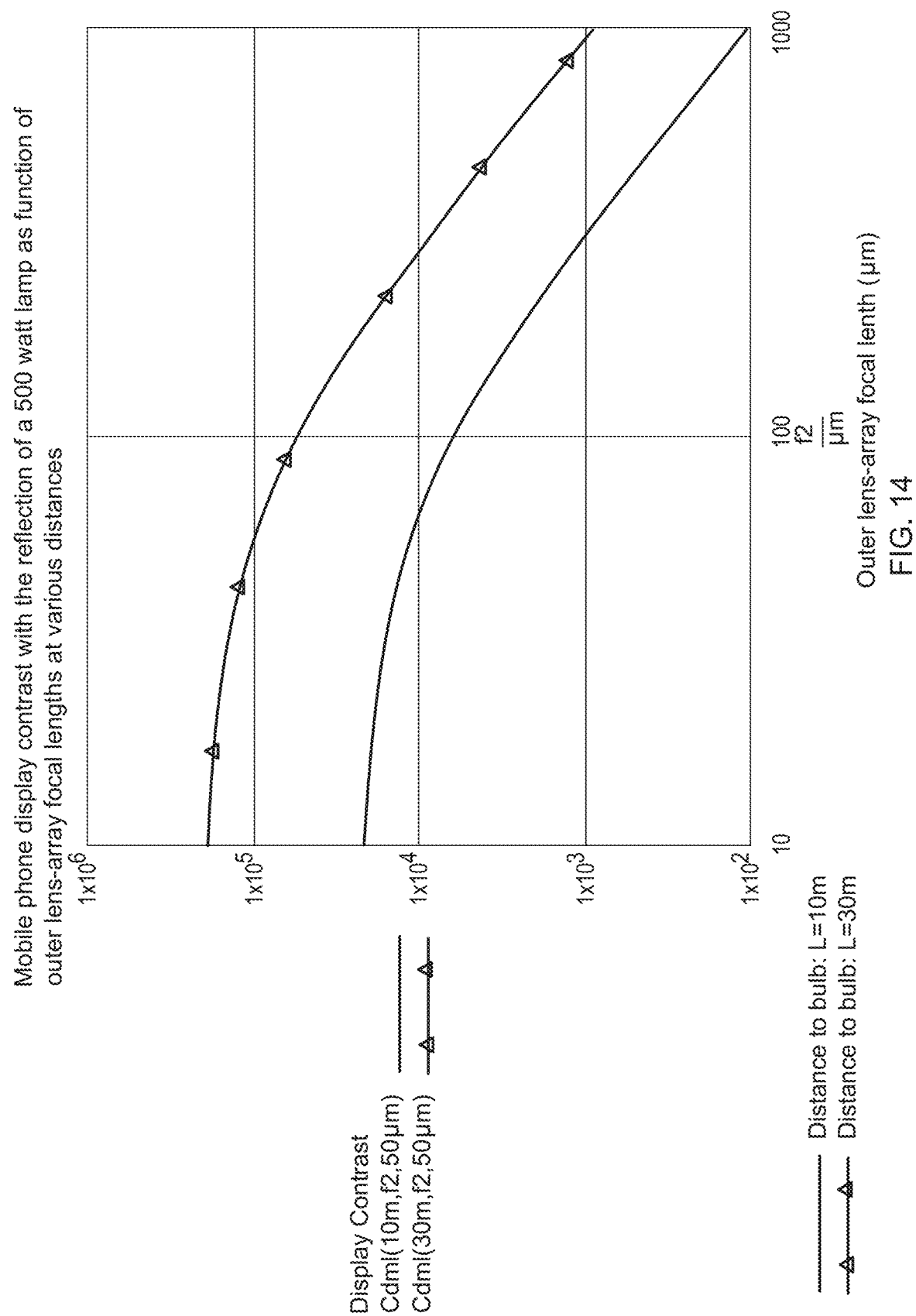
FIG. 14 presents the contrast as a function of the focal length f2 of the outer lens for different L.
Figure 16:
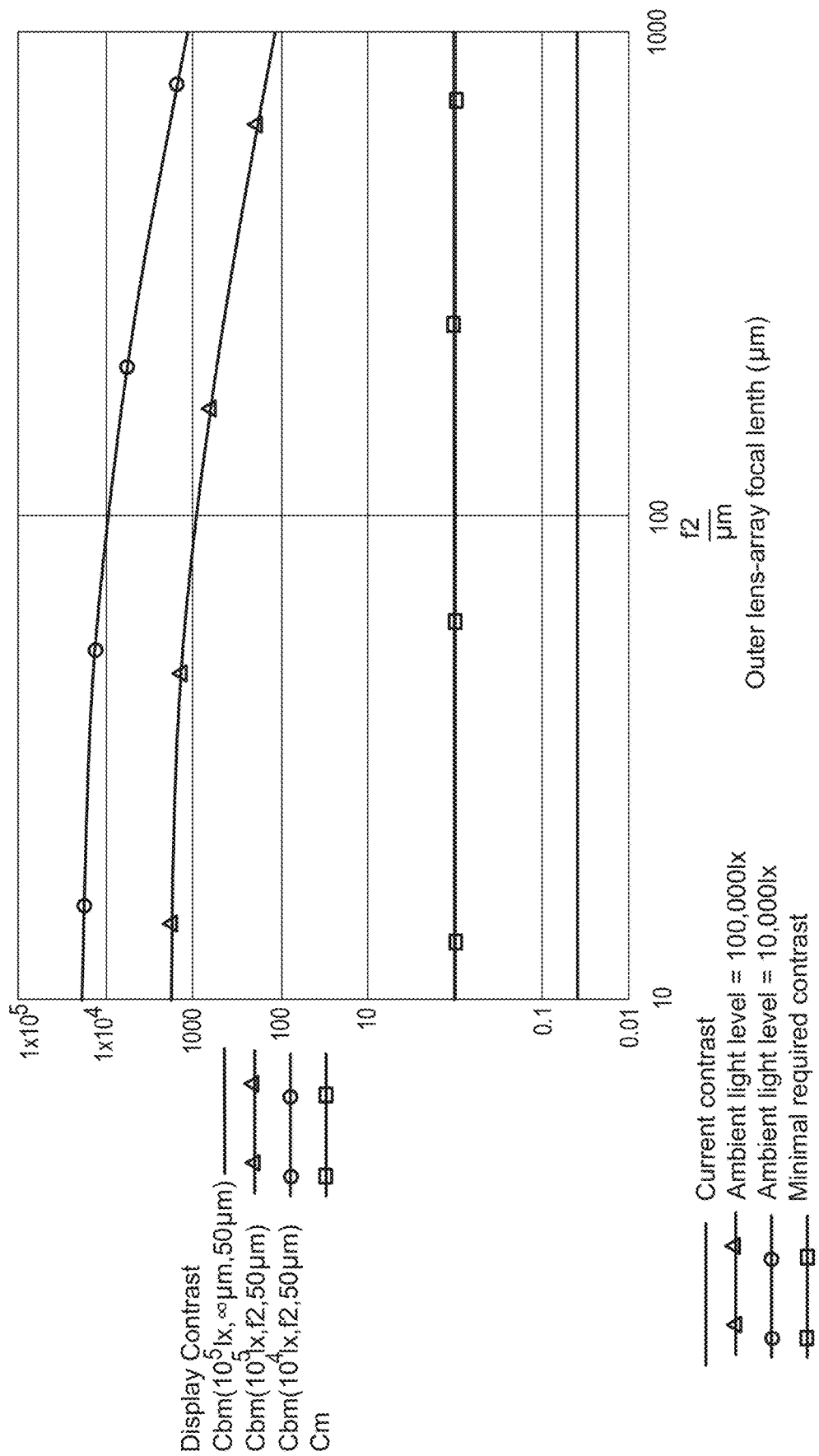
FIG. 16 presents the contrast of the display at the border of a reflected one dimensional step function in ambient light as a function of the focal length f2 of the outer lens for different ambient light intensities of Ib.

We will compare the light intensity that it forms on the retina of eye, when it is reflected and scattered from the lens array (right side on FIG. 6), to that of the current reflection of a flat, minor-like cover glass (left side of FIG. 6). For simplicity, we ignore transmission losses that anyway, cancel out.

The point source from a distance L is reflected from the cover glass (on the left) and from the lens array (on the right) onto the eye that is at a distance Le and focus on its retina. Usually, L>>Le Assume De is the diameter of the pupil of the eye.

The pupil of the eye subtends a solid angle of $$\frac{\pi De^2}{4(L+Le)^2}$$

The radiant power that enters into the eye is then:

$$Pe = Bs * \frac{\pi De^2}{4(L+Le)^2} = \frac{Ps}{4\pi} * \frac{\pi De^2}{4(L+Le)^2}$$

$$Pe = \frac{Ps * De^2}{16(L+Le)^2}$$

The image of that point source, reflected from the cover glass of the display, on the retina is effectively spread out on a circle with a diameter of the PSF (Point Spread Function) of the eye.

The area of the PSF on the retina is:

$$Ar = \frac{\pi}{4}(fe*\theta e)^2$$

where fe is the focal length of the lens of the eye and θe is its angular acuity (resolution). fe*θe is the effective diameter of that PSF.

Thus the Intensity of that point source on the retina of the eye is:

$$Ir = \frac{Pe}{Ar}$$

Substituting for Pe and Ar and rearranging, we get the expression for the retinal radiant intensity of a distant point source emitting a radiant power of Ps:

$$Ir = \frac{PsDe^2}{4\pi(L+Le)^2(fe\theta e)^2}$$

Now, in order to estimate the retinal radiant intensity of the same point source, reflected and scattered from the lens array, we first calculate the radiant power that impinges on one lens (cell) of the lens array.

Similar to the calculation above, that lens subtends a solid angle of $$\frac{\pi Dc^2}{4L^2}$$

where Dc is its diameter.

Thus, as calculated above, the fraction of the radiant power that impinges on a single lens of the lens array is:

$$Pc = Bs * \frac{\pi Dc^2}{4L^2} = \frac{Ps}{4\pi} * \frac{\pi Dc^2}{4L^2} = \frac{PsDc^2}{16L^2}$$

The solid angle of the eye, when viewed from the reflecting surface of the lens is $$\frac{\pi De^2}{4Le^2}$$

As discussed above (FIG. 5), the reflected light from the surface of the lens, spreads into a full cone angle of 2θm thus its effective area at the plane of the pupil of the eye, that is at a distance of Le is: $\pi(Le\theta m)^2$. The area of the pupil of the eye is $\pi/4 De^2$ Thus, the fraction of the radiant power that enters the eye is then approximately:

$$Pec = Pc \frac{\frac{\pi}{4}De^2}{\pi(Le\theta m)^2} = Pc \frac{De^2}{4(Le\theta m)^2} = \frac{PsDc^2}{16L^2} \frac{De^2}{4(Le\theta m)^2} = \frac{PsDc^2 De^2}{64L^2(Le\theta m)^2}$$

The image of this point source is spread-out on a circle with an effective diameter of the PSF of the eye thus, its intensity on the retina is:

$$Irc = \frac{Pec}{\frac{\pi}{4}(fe*\theta e)^2} = \frac{\frac{PsDc^2De^2}{64L^2(Le\theta m)^2}}{\frac{\pi}{2}(fe*\theta e)^2}$$

and following cancellations and rearrangement we get:

$$Irc = \frac{PsDc^2De^2}{16\pi L^2(Le\theta m)^2(fe*\theta e)^2}$$

As the size of the lens (cell), is below the resolution of the eye, the reflected intensities of adjacent cells in a circle that has the diameter of the PSF add up on the retina. The diameter of the PSF at the plane of the lens array is $Le*\theta e$ therefore, the number of cells that add up inside the PSF circle is approximately:

$$\left(\frac{Le*\theta e}{Dc}\right)^2$$

thus, the reflected intensity on the retina is:

$$Irm = Irc\left(\frac{Le*\theta e}{Dc}\right)^2 = \frac{PsDc^2De^2}{16\pi L^2(Le\theta m)^2(fe*\theta e)^2}\left(\frac{Le*\theta e}{Dc}\right)^2$$

Following cancellations of similar parameters and rearrangements we get the reflected radiant intensity, of the point source, from the lens array on the retina:

$$Irm = \frac{PsDe^2}{16\pi L^2 \theta m^2 fe^2}$$

Finally, we divide the retinal intensity reflected from the lens array by the one reflected from the original flat cover glass, in order to get the improvement ratio of the lens array in suppressing the obstructing reflection of the ambient point source:

$$\frac{Irm}{Ir} = \frac{\frac{PsDe^2}{16\pi L^2 \theta m^2 fe^2}}{\frac{PsDe^2}{4\pi(L+Le)^2(fe\theta e)^2}} = \frac{(L+Le)^2}{4L^2}\left(\frac{\theta e}{\theta m}\right)^2 = \left(1+\frac{Le}{L}\right)^2\left(\frac{\theta e}{2\theta m}\right)^2$$

As mentioned above, in usual display viewing scenarios: L>>Le therefore $$\frac{Le}{L}$$

may be neglected compared to 1 so we finally get the lens array matte suppression ratio of a reflected background point source:

$$\frac{Irm}{Ir} \sim \left(\frac{\theta e}{2\theta m}\right)^2$$

This means that the peak intensity of the reflected image of the ambient point source is lowered by a factor of $$\left(\frac{\theta e}{2\theta m}\right)^2$$

due to the matte effect of the lens array.

The radius of the surface of the lens is related to $\theta m$ and Dc, the dimension of the cell by:

$$R = \frac{Dc}{2\tan\frac{\theta m}{2}}$$

thus, $$\theta m = 2\tan^{-1}\frac{Dc}{2R}.$$

Substituting in the above equation one gets the improvement factor in suppression of a reflected background point source, in terms of Dc—the cell size and R—the radius of curvature of the outer surface of the lens:

$$\frac{Irm}{Ir} \sim \left(\frac{\theta e}{4\tan^{-1}\frac{Dc}{2R}}\right)^2$$

A similar calculation was performed for the case of a square cell. The contrast improvement factor is very similar:

$$\frac{Irm}{Ir} \sim \left(\frac{\pi\theta e}{8\theta m}\right)^2$$

Example:
Assume:
$\theta e = 3*10^{-4}$ Rad (the visual acuity of the eye)
Dc=100 μm
R=1000 μm $$\Rightarrow \frac{Irm}{Ir} = 3.5*10^{-6}$$

This means that the reflection of that point source is spread out and its peak intensity is lowered by more than 5 orders of magnitude thus the contrast of the reflected image is lowered by that amount and this is also the increase in the display contrast thus it is not obstructing the observer any more.

Following are the calculations that present the expected contrast improvement of the display, for various types of ambient background reflections. The radius R is represented by f2, the focal length of the outer surface of the lens in the lens array. It is related to R through the relation: $R=(n-1)f2$ where n is the refractive index.

As previously calculated, the contrast of a reflected small or "point source" from the lens array is decreased by the square of the increase ratio of the angles $$\left(\frac{\theta e}{2\theta m}\right)^2$$

because its energy spread is two dimensional.

One may assume that each extended source is an ensemble of point sources thus, the following calculations uses this assumption to assess the improvement of the proposed "lens-array matte display" contrast for reflected extended sources. In the more general case, most of the ambient reflected images comprise contrast step function changes across one dimensional borders thus, the above mentioned spread in energy is only one dimensional therefore, the "lens-array matte display" improvement factor, is only linear in that angles ratio thus:

$$\frac{Irm}{Ir} \sim \left(\frac{\theta e}{2\theta m}\right)$$

In FIGS. 8, 9, 10 and 11, we present the contrast improvement for three cases; Point source, a bulb source and a line step source.

Current Standard Display Contrast:

In order to assess the current contrast of a display with a plane cover glass when viewed under strong ambient light conditions, we assume the following:

1. The light emitted by the display has approximately a Lambertian resolution.
2. The brightness of the display is Bd.
3. The cover glass of the display is plane and its reflectance is Rd.
4. The ambient light intensity is Ib.
5. The reflected ambient image blends with the desired displayed image and disrupts it.
6. The contrast between the displayed image and the reflected one may be estimated by the following:

$$C_0 = \frac{Bd}{\pi RD Ib}$$

7. The higher this contrast is, the better is the quality of the displayed image under ambient illumination.
8. We may assume that there is a minimal contrast between these two images that is still acceptable. Without loss of generality, we may assume that this minimal contrast is: $C_m=1$ Referring to 550 in FIG. 4 we will present few examples of how one can design an optical sub system that is attached to the micro lenses array at the outer layer that is composed of convex or concave micro lens array. This configuration of 550 with 570 provides a pass-through for the display image without distortion and improves significantly the contrast.

There are various types of apparatuses that may provide a matte affect without substantially distorting the image of the display. These types are illustrated below.

Zero Power Micro Lens Array

Figure 17:
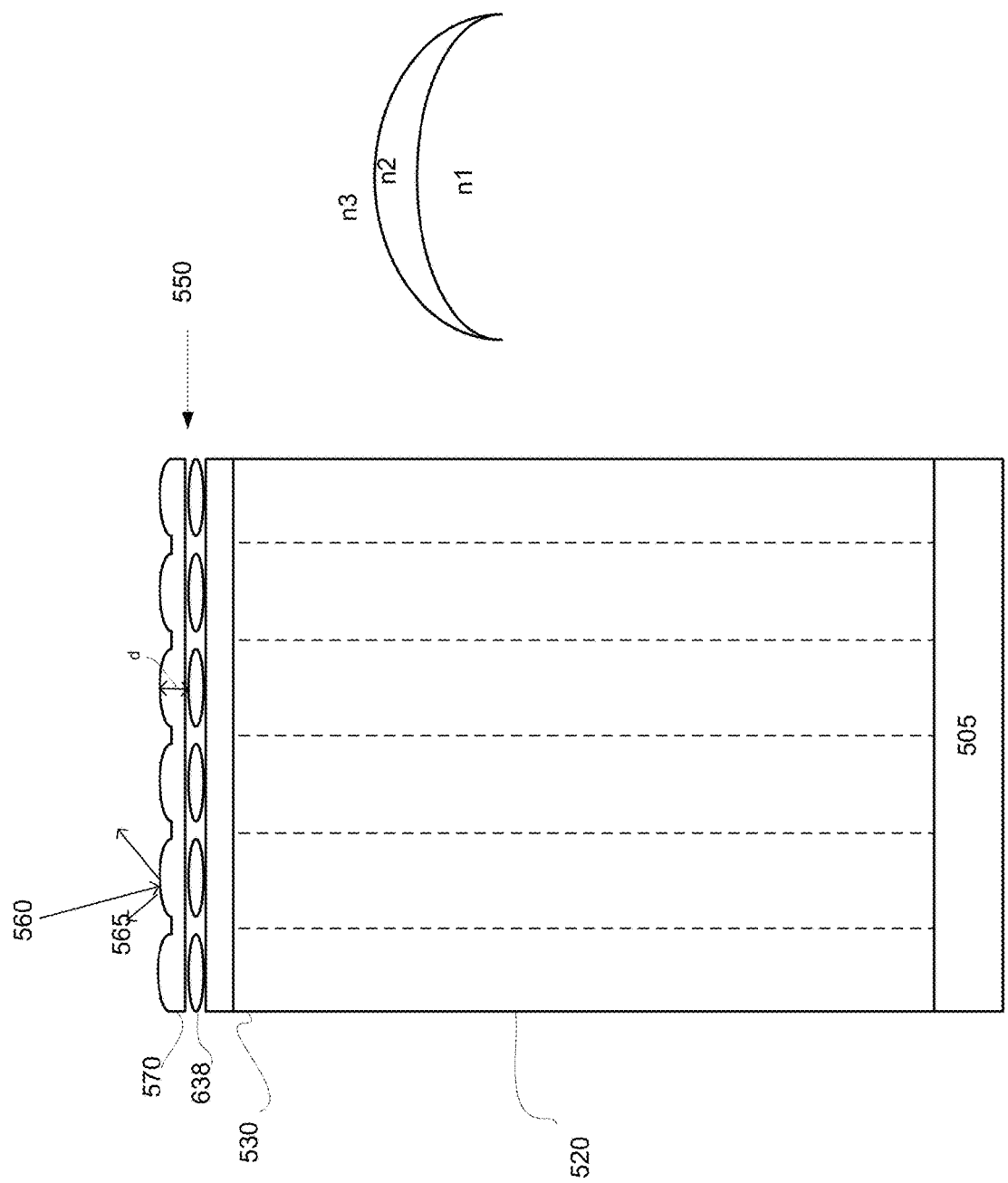
FIG. 17 is an example of an apparatus.

FIG. 17 presents a one dimensional cross section of a two dimensional micro structured of zero power lens array, namely the upper micro lens array layer 570 with the sub optical system 550 and the transparent index matching glue/gel 530 provides a "Zero-Power" lens array. Each small cell is composed of a transparent dielectric material that is confined between two partially spherical boundaries. One example of a "Zero-Power" lens is also shown in FIG. 17. In the case that on both of its sides there is a transparent material with the same refractive index such as air n1=n3=1, it comprises a thin shell of transparent material between 2 identical radii. The transparent index matching glue/gel 530 contacts display glass 520.

In the general case the boundaries of the lens confine 3 different transparent materials with refractive indexes of n1, n2, and n3. In this case, the radii will depend on the refractive indexes but will form a combined lens with a zero power and therefore, an infinite focal length Following are the formulas that control the dimensions and radii of the "Zero Power Micro Lens Array (ZPMLA):

The optical power P1, of the inner, $1^{st}$ surface is given by the formula:

$$P1 = \frac{n2 - n1}{R1}$$

Where n1 and n2 are the refractive indexes on both sides of the spherical surface with a radius of R1.

Similarly, the optical power of the outer, $2^{nd}$ surface is given by the formula:

$$P2 = \frac{n3 - n2}{R2}$$

Where n2 and n3 are the refractive indexes on both sides of the spherical outer surface with a radius of R2.

The combined optical power, of both surfaces, P is given by the formula:

$$P = P1 + P2 - P1 * P2 * \frac{d}{n2}$$

Where d is the distance between both surfaces.

The condition for "Zero power" translates to the requirement that: P=0 Choosing the radius of the $1^{st}$, inner surface R1 and the distance d between the two surfaces and solving $$P = P1 + P2 - P1 * P2 * \frac{d}{n2} = 0$$

For R2, results in the following formula:

$$R2 = \frac{n3 - n2}{n2} * d - \frac{n3 - n2}{n2 - n1} * R1$$

Since the focal length f, of this compound lens is given by: f=1/P, this focal length approaches Infinity: f=∞.

Following is a practical example that uses parameters of real transparent dielectric materials that match production limitations:

n1=1.62, $1^{st}$ transparent material
n2=1.52, $2^{nd}$ transparent material
n3=1, Air
R1=80 μm, $1^{st}$ spherical surface
d=20 μm, the distance between the surfaces Substituting the parameters in the formula above results in the required outer radius R2: R2=409 µm In the "Zero power lens array" approach, the power of the 1st surface is accompanied by the $2^{nd}$ surface with an opposite power that cancels the power of the $1^{st}$ surface thus, forming a zero power lens element. A lens that has a zero power, does not change the image of an object viewed through it and acts like a plane glass.

When a display will be viewed through such a "Zero-Power" micro-lens array and the individual lenses are smaller than 150 um, below the resolving power of the eye, it will appear unaltered, as if viewed through the current clear glass cover. Such a "Zero-Power" lens array may be a perfect matte scattering surface for the reflected ambient image, effectively reducing its contrast to zero but allowing us to view the display behind it with no change or damage to its resolution. If one wants further to reduce the ambient light effect he may add well known anti-reflective coating on 570. The coating is very thin (few Nano meters) and does not affect the performance of 570.

A typical cell size, with the above mentioned requirements and production limitations will be: Dc=50 µm.

The typical thickness of the display and cover glass us 1-1.5 mm. The exact thickness of the display and cover glass does not affect the performance of the ZPMLA because its optical power is Zero.

2. "Keplerian Telescope" Lens Array

Figure 18:
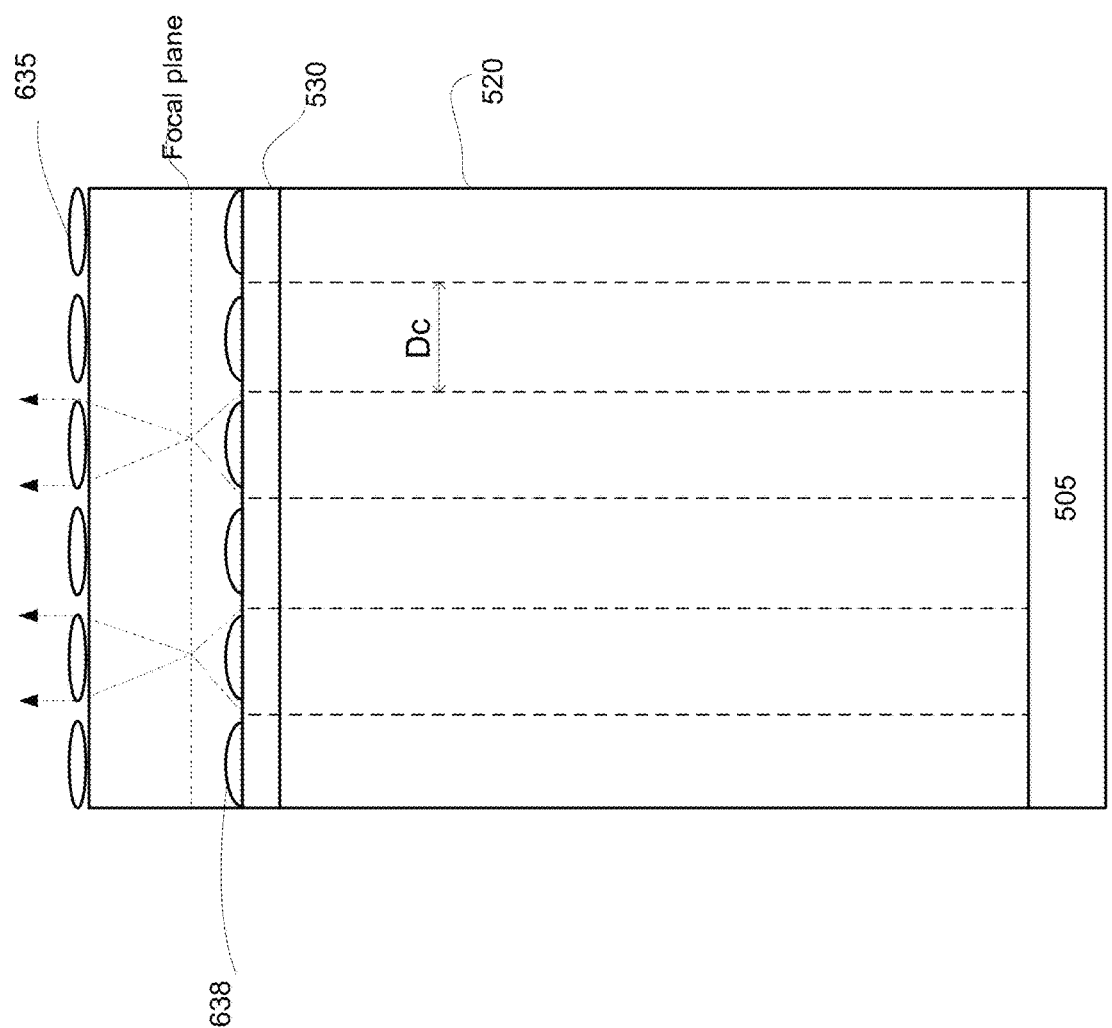
FIG. 18 is an example of an apparatus.

FIG. 18 presents one dimensional cross section of a two dimensional micro structured array of Keplerian telescopes, namely each telescope is composed of two positive lenses one on each side. FIG. 18 illustrates an apparatus that may include transparent index matching glue/gel 530, and layer of positive lenses, each with a focal length of f1, that form the inner lens array 638. On top of that layer, there is an outer lens array of positive lenses 635 with focal length f2 that re-collimate the light to provide the desired FOV. The dimensions of f1 and f2 are in the µm range but need to be determined by optical ray tracing in order to optimize the image on the retina of the eye of the observer. A typical cell size may be: Dc=20-100 µm and the overall thickness of the MLA foil will be of the order of f1+f2. Typical values may be: f1=50 µm, f2=500 µm and a total net foil thickness of about 550 µm. The transparent index matching glue/gel 530 contacts display glass 520.

Due to the repetitive nature of the lens array and the fact that each element is below the user eye resolution, a matte effect is achieved which diffuse the ambient light. It must be noted that in this configuration the matte effect do not blur the image, this is due to fact that the telescope reimages the display 505 outside of the apparatus without distortion the display image.

This configuration provides an apparatus that from the ambient point of view, acts as a perfect matte surface namely, minimal reflection to the user's eye, however from the display point of view the display is reimaged to the eye of the observer without distortion. This is very attractive since the ambient image and light that currently, are reflected to the eye of the user and obstruct the displayed image, are strongly diffused while the image of the display remains sharp and clear. The apparatus and system that is described in this application allows us to improve significantly the contrast of the display in the presence of strong ambient light at the background without sacrificing the resolution of the displayed image.

If one wants further to reduce the ambient light effect he may add well known anti-reflective coating on 635. The coating is very thin (few Nano meters) and does not affect the performance of 635.

3. Keplerian Telescope Lens Array with Black Walls

Figure 19:
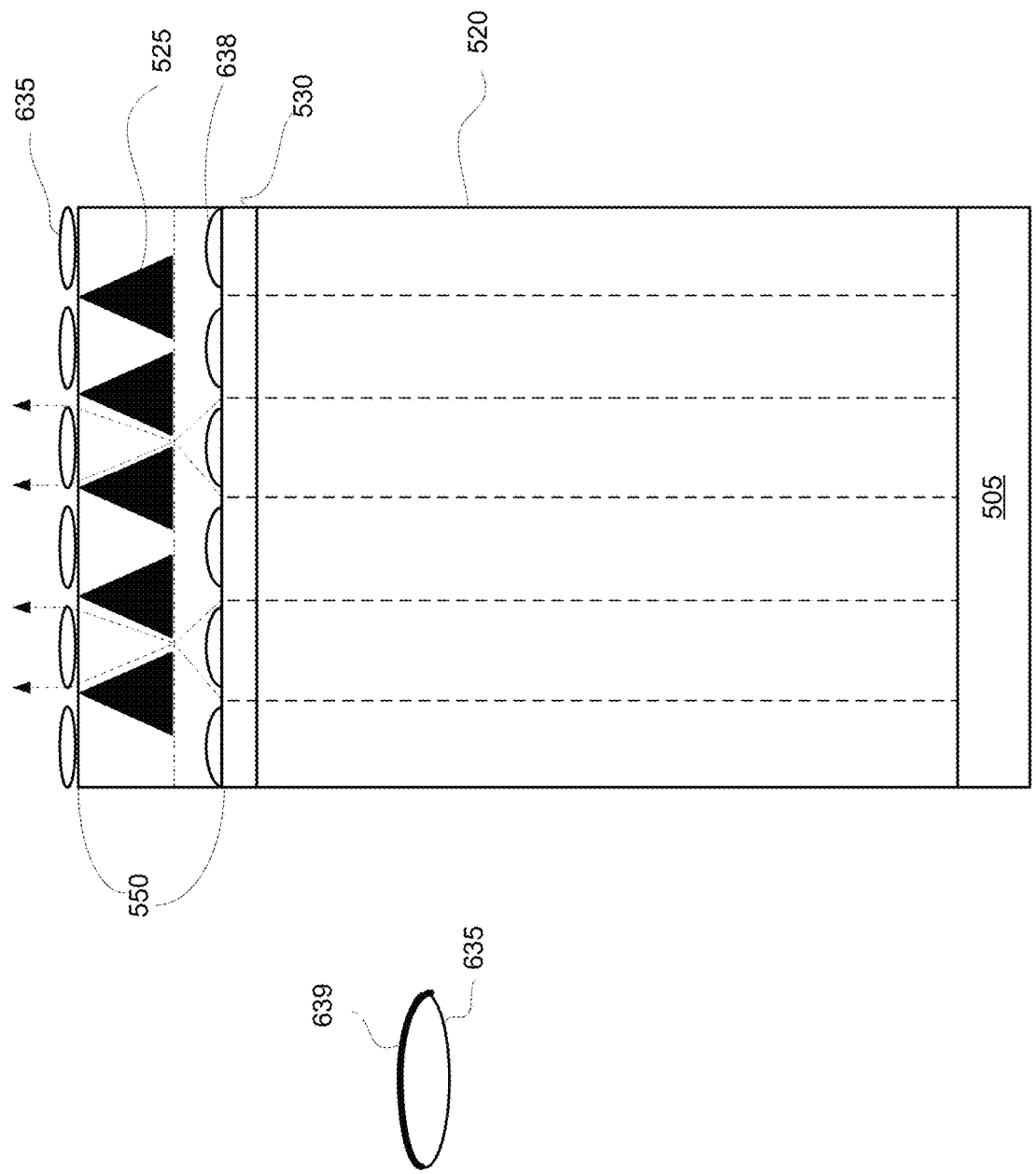
FIG. 19 is an example of an apparatus.

FIG. 19 presents a one dimensional cross section of a two dimensional micro structured array of Keplerian telescopes similar to FIG. 18 but with spatial filters 525. FIG. 19 illustrates an apparatus that includes a transparent index matching glue/gel 530 and positive layer of lens array 638, spatial filters 525 may be arranged in a layer layer and may be black walls (or spatial filters of other shape and/or size), which preserve the image resolution as well as blocks the penetrated ambient light. The spatial filters prevent crosstalk between adjacent cells. On top of spatial filters 525 there is another array of positive lenses 635 with focal length f2, that re-collimate the light to provide the desired FOV. The transparent index matching glue/gel 530 contacts display glass 520. FIG. 19 also illustrates a nanometric scale anti-reflective coating 639 deposited on microlens 635

The dimensions of f1 and f2 are in the µm range but need to be determined by optical ray tracing in order to optimize the image on the retina of the eye of the observer. A typical cell size may be: Dc=20-100 µm and the overall thickness of the MLA foil will be of the order of f1+f2.

Typical values may be: f1=50 µm, f2=500 µm and a total net foil thickness of about 550 µm.

Due to the repetitive nature of the lens array and the fact that each element is below the user eye resolution, a matte effect is achieved which diffuse the ambient light. It must be noted that in this configuration the matte effect do not blur the image, as the telescope reimage the display image to eye of the user with minimal crosstalk between adjacent pixels. This configuration provides an apparatus that from the ambient point of view it acts as a matte display namely, it diffuses the ambient image reflection to the user's eye, however from the display point of view the display image reimaged to user's eye without distortion. This is very attractive since the ambient light is strongly diffused while the image remains sharp and clear. The apparatus and system that is described in this invention allow us to improve significantly the contrast of the display in the presence of a strong ambient light at the background without sacrificing the resolution of the displayed image.

Galilean Binocular Lens Array

If one wants further to reduce the ambient light effect he may add well known anti-reflective coating on 635. The coating is very thin (few Nano meters) and does not affect the performance of 635.

Figure 20:
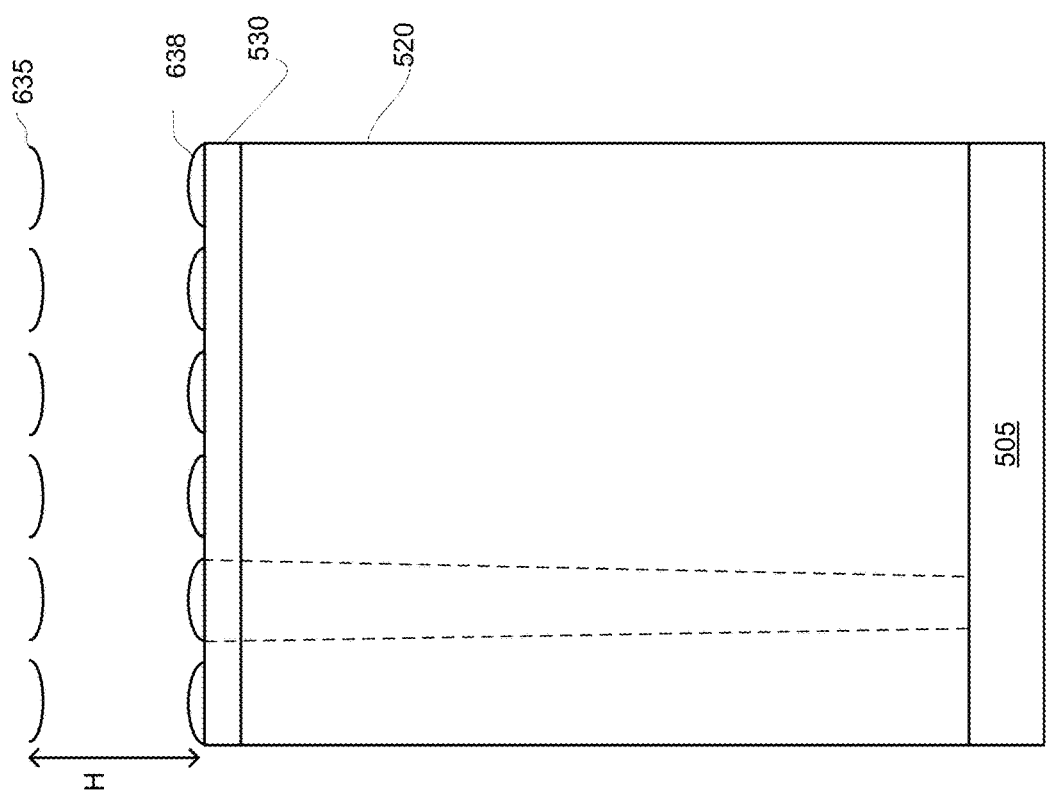
FIG. 20 is an example of an apparatus.

FIG. 20 presents a one dimensional cross section of a two dimensional micro structured array of Galilean binocular arrangement, namely each telescope is composed of one positive and one negative lenses each on each side. FIG. 20 illustrates an apparatus that may include a transparent index matching glue/gel 530 layer and a positive lens array 638. The transparent index matching glue/gel 530 contacts the apparatus to the display glass 520.

On top of layer we add an array of negative lenses 635 with focal length f2 that re-collimate the light to provide the desired FOV. In a case where f1 and f2 have a common focus, all the outgoing rays from a display point on the optical axis of the cell will be parallel.

The dimensions of f1 and f2 are in the µm range but need to be determined by optical ray tracing in order to optimize the image on the retina of the eye of the observer. A typical cell size may be: Dc=20-100 µm and the overall thickness of the MLA foil will be of the order of f1-f2.

Typical values may be: f1=500 µm, f2=50 µm and a total net foil thickness of about 450 µm.

Due to the repetitive nature of the negative lens array and the fact that each element is below the user eye resolution, a matte effect is achieved which diffuse the ambient light. It must be noted that in this configuration the matte effect does not blur the image, this is due the fact that the display image is reimaged by each binocular cell without distortion.

This configuration provides an apparatus that from the ambient point of view, acts as a matte display namely minimal reflection to the user eye, however from the display point of view the display image is reimaged to the eye of the observer without distortion. This is very attractive since the reflected ambient image and light are strongly diffused while the image remains sharp and clear. The apparatus and system that is described in this application allow us to improve significantly the contrast of the display in the presence of a strong ambient light at the background without sacrificing the resolution of the displayed image.

A similar configuration but with an opposite configuration may be applied namely, the inner micro lens array may comprise negative lenses while the outer micro lens array is positive.

Galilean Telescope Binocular Lens Array with Spatial Filters

If one wants further to reduce the ambient light effect he may add well known anti-reflective coating on 635. The coating is very thin (few Nano meters) and does not affect the performance of 635.

Figure 21:
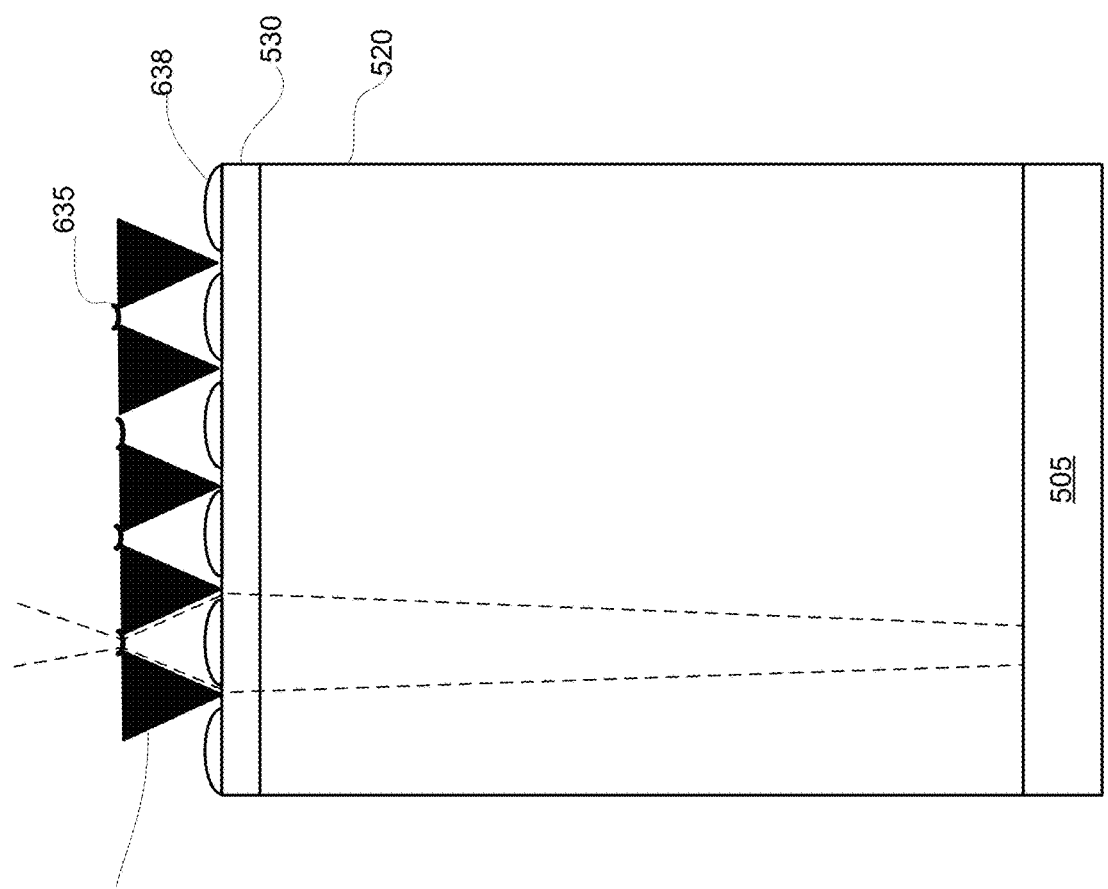
FIG. 21 is an example of an apparatus.

FIG. 21 presents one dimensional cross section of a two dimensional micro structured array of Galilean telescopes, with spatial filters 525. FIG. 21 illustrates an apparatus that may include a layer of positive lens array 638. The spatial filters 525 may be made of black walls array, which blocks the penetrated ambient light and preserves the image resolution. This is due the fact that this configuration acts as an array of spatial filters thus preventing crosstalk between adjacent cells. On top of spatial filters 525 there is an array of negative lenses 635 with focal length f2 that re-collimate the light to provide the desired FOV. In a case where f1 and f2 have a common focus, all the outgoing rays from a display point on the optical axis of the cell will be parallel and perpendicular to the display. The apparatus also includes a transparent index matching glue/gel 530 that contacts display glass 520.

If one wants further to reduce the ambient light effect he may add well known anti-reflective coating on 635. The coating is very thin (few Nano meters) and does not affect the performance of 635.

Figure 22:
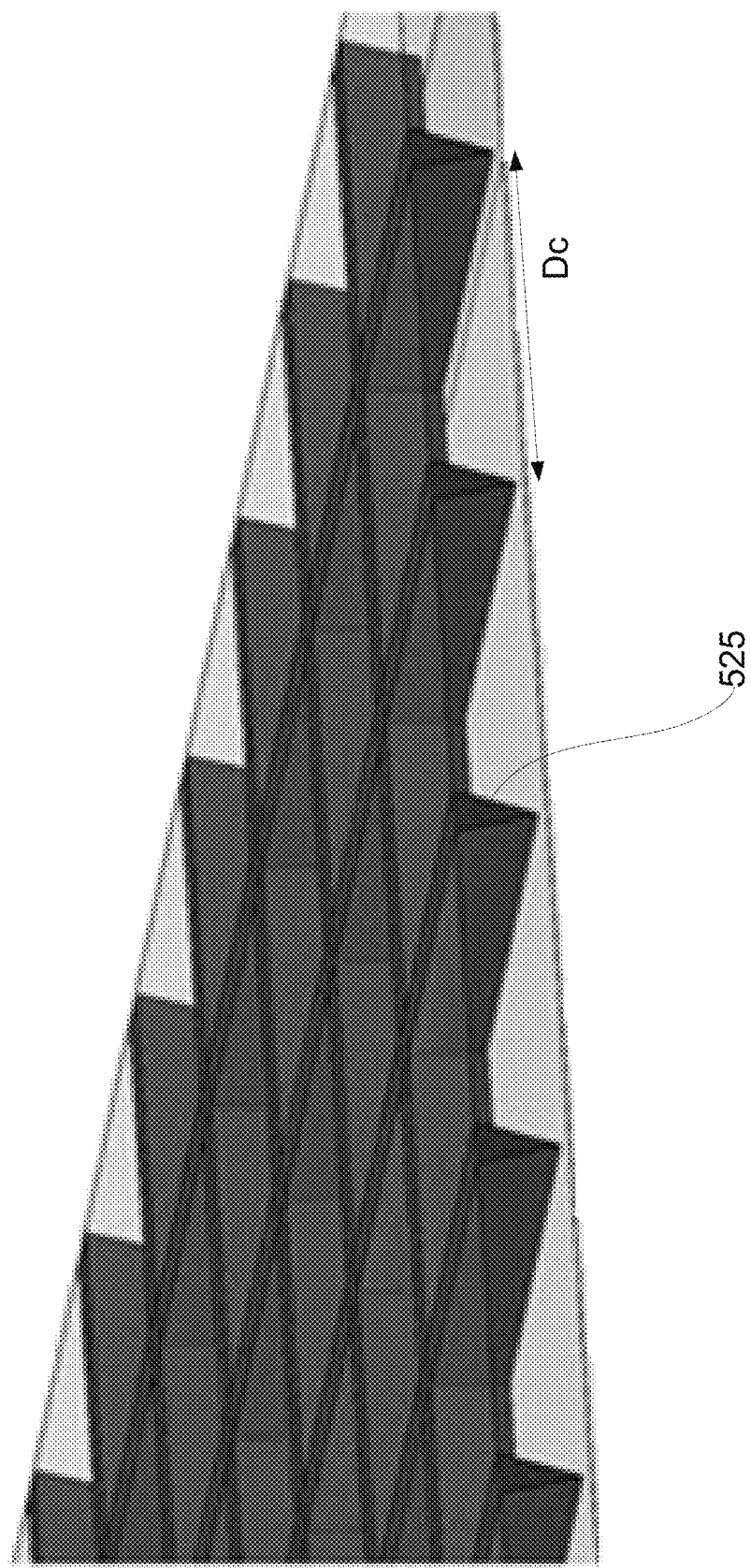
FIG. 22 is an example of one or more parts of an apparatus and of a display.

FIG. 22 illustrates an array of spatial filters 525.

FIG. 23 illustrates method 900.

Method 900 is for providing a matte affect while enhancing an output of a display that comprises multiple display pixels.

Method 900 includes steps 910 and 920.

Step 910 of scattering ambient light, by a first array of microlenses that is configured to scatter ambient light.

Step 920 of imaging, by the first array of microlenses and by a second array of microlenses the display onto the eye of the user, when the apparatus is attached to the display. The first array of microlenses is parallel to the second array of microlenses. Microlenses of the first array of microlenses and the microlenses of the second array have dimensions of tens of microns.

Step 920 may be executed without introducing distortions and loss of resolution that are sensed by a human eye.

Any of the mentioned above apparatuses may include an anti-reflective coating having a nanometric scale thickness that may be disposed on an exterior of the microlenses of the first array of microlenses.

The apparatus may include more than two arrays of microlenses—there may multiple arrays of microlenses arranged in different layers—including the first array of microlenses, the second array of microlenses and one or more additional arrays of microlenses between the first and second arrays of microlenses. In this case microlenses of the multiple arrays of microlenses may have a dimension of tens of microns. Furthermore—the multiple arrays of microlenses are shaped and positioned to pass through the image from the display, when the apparatus is attached to the display.

In the detailed description, numerous specific details are set forth in order to provide a thorough understanding of the apparatus and method. However, it will be understood by those skilled in the art that the present apparatus and method may be practiced without these specific details.

In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to an apparatus capable of executing the method.

Any reference in the specification to an apparatus should be applied mutatis mutandis to a method that may be executed by the apparatus.

The term "and/or" is additionally or alternatively.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components.

Likewise, any two components so associated can also be viewed as being "operably connected," or "operably coupled," to each other to achieve the desired functionality. Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

The phrase "may be X" indicates that condition X may be fulfilled. This phrase also suggests that condition X may not be fulfilled. For example—any reference to a apparatus as including a certain component should also cover the scenario in which the apparatus does not include the certain component.

The terms "including", "comprising", "having", "consisting" and "consisting essentially of" are used in an interchangeable manner. For example—any method may include at least the steps included in the figures and/or in the specification, only the steps included in the figures and/or the specification. The same applies to the apparatus and the mobile computer.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one as or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements the mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Any combination of any component of any component and/or unit of apparatus that is illustrated in any of the figures and/or specification and/or the claims may be provided.

Any combination of any apparatus illustrated in any of the figures and/or specification and/or the claims may be provided.

Any combination of steps, operations and/or methods illustrated in any of the figures and/or specification and/or the claims may be provided.

Any combination of operations illustrated in any of the figures and/or specification and/or the claims may be provided.

Any combination of methods illustrated in any of the figures and/or specification and/or the claims may be provided.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

We claim:

1. An apparatus for providing a matte affect while enhancing an output of a display that comprises multiple display pixels, the apparatus comprises:
    a first array of microlenses that is configured to scatter ambient light;
    a second array of microlenses; and
    an array of spatial filters that are positioned between the first array of microlenses and the second array of microlenses; wherein each spatial filter has a minimal thickness of microscopic scale;
    wherein first array of microlenses is parallel to the second array of microlenses;
    wherein microlenses of the first array of microlenses and the microlenses of the second array have a dimension of tens of microns;
    wherein the first array of microlenses and the second array of microlenses are shaped and positioned to pass through the image from the display, when the apparatus is attached to the display; and
    wherein multiple microlenses of the first array of microlenses and multiple lenses of the second array of microlenses form multiple Galilean telescopes lenses.

2. The apparatus according to claim 1 wherein the apparatus is configured to pass through the image from the display without introducing distortions and loss of resolution that are sensed by a human eye.

3. The apparatus according to claim 1 wherein the apparatus has zero optical power.

4. The apparatus according to claim 1 wherein a distance between the first array of microlenses and the second array of microlenses is in the range between ten and a few hundred micrometers.

5. The apparatus according to claim 1 wherein a focal plane of microlenses of the first array of microlenses and the focal plane of microlenses of the second array of microlenses overlap.

6. The apparatus according to claim 5 wherein a distance between the first array of microlenses and the second array of microlenses ranges between ten and a few hundred micrometers.

7. The apparatus according to claim 1 wherein a gap between the first array of microlenses and the second array of microlenses is filled only by one or more transparent materials.

8. The apparatus according to claim 1 comprising an anti-reflective coating on lenses of the first array of microlenses.

9. A method for providing a a matte affect while enhancing an output of a display that comprises multiple display pixels, the method comprises:
scattering ambient light, by a first array of microlenses that is configured to scatter ambient light;
passing through, by the first array of microlenses and by a second array of microlenses, of the image from the display, when the apparatus is attached to the display;
preventing cross talks between adjacent cells, by an array of spatial filters that are positioned between the first array of microlenses and the second array of microlenses; wherein each spatial filter has a minimal thickness of microscopic scale; wherein each cell comprises a microlens array of the first array of microlenses and a microlens array of the second array of microlenses; wherein the first array of microlenses is parallel to the second array of microlenses; wherein microlenses of the first array of microlenses and the microlenses of the second array have dimensions of tens of microns; wherein multiple microlenses of the first array of microlenses and multiple lenses of the second array of microlenses form multiple Galilean telescopes lenses.

10. The method according to claim 9 wherein the passing through is executed without introducing distortions and loss of resolution that are sensed by a human eye.

11. The method according to claim 9 wherein a distance between the first array of microlenses and the second array of microlenses is in the range between ten and a few hundred micrometers.

12. The method according to claim 9 wherein a focal plane of microlenses of the first array of microlenses and the focal plane of microlenses of the second array of microlenses overlap.

13. The method according to claim 12 wherein wherein a distance between the first array of microlenses and the second array of microlenses ranges between ten and a few hundred micrometers.

14. The method according to claim 9 wherein a gap between the first array of microlenses and the second array of microlenses is filled only by one or more transparent materials.

15. The method according to claim 9 wherein the lenses of the first array of microlenses are coated with an anti-reflective coating.

16. The method according to claim 9 wherein the method is executed by an apparatus that has zero optical power.

* * * * *